US012678277B2

(12) United States Patent
Lederman et al.

(10) Patent No.: US 12,678,277 B2
(45) Date of Patent: Jul. 14, 2026

(54) SYSTEMS AND METHODS FOR MITRAL VALVE REPLACEMENT

(71) Applicant: The USA, as represented by the Secretary, Department of Health and Human Services, Bethesda, MD (US)

(72) Inventors: Robert J. Lederman, Chevy Chase, MD (US); Toby Rogers, Washington, DC (US)

(73) Assignee: THE USA, AS REPRESENTED BY THE SECRETARY, DEPT. OF HEALTH AND HUMAN SERVICES, Bethesda, MD (US)

( * ) Notice: Subject to any disclaimer, the term of this patent is extended or adjusted under 35 U.S.C. 154(b) by 720 days.

(21) Appl. No.: 18/006,331

(22) PCT Filed: Jul. 20, 2021

(86) PCT No.: PCT/US2021/042380
§ 371 (c)(1),
(2) Date: Jan. 20, 2023

(87) PCT Pub. No.: WO2022/020357
PCT Pub. Date: Jan. 27, 2022

(65) Prior Publication Data
US 2023/0285143 A1     Sep. 14, 2023

Related U.S. Application Data

(60) Provisional application No. 63/054,623, filed on Jul. 21, 2020.

(51) Int. Cl.
*A61F 2/24* (2006.01)

(52) U.S. Cl.
CPC .......... *A61F 2/2418* (2013.01); *A61F 2/2415* (2013.01); *A61F 2/2457* (2013.01)

(58) Field of Classification Search
CPC .... A61F 2/2445; A61F 2/2457; A61F 2/2454; A61F 2/2427; A61F 2/246; A61F 2/2409;
(Continued)

(56) References Cited

U.S. PATENT DOCUMENTS

| 5,332,402 A | 7/1994 | Teitelbaum |
| 5,500,016 A | 3/1996 | Fisher |
(Continued)

FOREIGN PATENT DOCUMENTS

| EP | 2979665 A1 * | 2/2016 | .......... A61F 2/2415 |
| GB | 2513195 | 10/2014 | |
(Continued)

OTHER PUBLICATIONS

Extended Search Report for European Patent Application No. 21845838.8, dated Jul. 11, 2024 12 pages.
(Continued)

*Primary Examiner* — Seema Mathew
(74) *Attorney, Agent, or Firm* — Sheridan Ross P.C.

(57) ABSTRACT

Systems and methods of atrioventricular valve replacement are provided. In various embodiments, an arch-like support structure is provided that is insertable and implantable into a heart and is positioned in the mitral annulus to replace a native mitral valve. The support structure is operable to support, and various systems comprise leaflet and chord structures operable to control and regular blood flow between chambers of the heart.

20 Claims, 9 Drawing Sheets

(58) Field of Classification Search

CPC .... A61F 2/2442; A61F 2/2463; A61F 2/2448; A61F 2/2487; A61F 2/24; A61F 2/2496; A61F 2/2451

See application file for complete search history.

(56) References Cited

U.S. PATENT DOCUMENTS

| | | | |
|---|---|---|---|
| 5,554,184 A | 9/1996 | Machiraju | |
| 6,283,994 B1 | 9/2001 | Moe et al. | |
| 7,591,847 B2 | 9/2009 | Navia et al. | |
| 9,232,996 B2 | 1/2016 | Sun et al. | |
| 9,387,075 B2 | 7/2016 | Bortlein et al. | |
| 9,655,722 B2 | 5/2017 | Morris et al. | |
| 9,861,475 B2 | 1/2018 | Machold et al. | |
| 10,117,741 B2 * | 11/2018 | Schweich, Jr. | A61F 2/2409 |
| 10,376,365 B2 | 8/2019 | Khairkhahan | |
| 2003/0083742 A1 * | 5/2003 | Spence | A61F 2/2418 623/2.16 |
| 2005/0070999 A1 * | 3/2005 | Spence | A61F 2/2448 623/2.37 |
| 2005/0228495 A1 | 10/2005 | Macoviak | |
| 2006/0149368 A1 * | 7/2006 | Spence | A61F 2/2445 623/2.37 |
| 2008/0221672 A1 | 9/2008 | Lamphere et al. | |
| 2009/0012354 A1 * | 1/2009 | Wood | A61F 2/2487 600/37 |
| 2010/0217382 A1 | 8/2010 | Chau et al. | |
| 2010/0262233 A1 | 10/2010 | He | |
| 2012/0323313 A1 | 12/2012 | Seguin | |
| 2014/0343669 A1 | 11/2014 | Lane et al. | |
| 2014/0379095 A1 | 12/2014 | Waisblatt et al. | |
| 2015/0094802 A1 | 4/2015 | Buchbinder et al. | |
| 2016/0022254 A1 | 1/2016 | McCarthy | |
| 2016/0324639 A1 | 11/2016 | Nguyen et al. | |
| 2018/0263768 A1 * | 9/2018 | Zhang | A61F 2/2418 |
| 2019/0167422 A1 | 6/2019 | Guttenberg et al. | |
| 2019/0388220 A1 * | 12/2019 | Vidlund | A61F 2/2412 |
| 2020/0188097 A1 * | 6/2020 | Perrin | A61F 2/2433 |
| 2021/0196462 A1 * | 7/2021 | Khairkhahan | A61F 2/2445 |
| 2021/0298896 A1 * | 9/2021 | Pham | A61F 2/2463 |

FOREIGN PATENT DOCUMENTS

| | | | | |
|---|---|---|---|---|
| WO | WO 2016/178126 | 11/2016 | | |
| WO | WO 2019/157331 | 8/2019 | | |
| WO | WO-2019147585 A1 * | 8/2019 | | A61L 27/507 |
| WO | WO-2022120157 A1 * | 6/2022 | | A61F 2/2457 |

OTHER PUBLICATIONS

Black et al. "A Three-Dimensional Analysis of a Bioprosthetic Heart Valve," Journal of Biomechanics, 1991, vol. 24, No. 9, pp. 793-801.

Black et al. "Mechanical and Other Problems of Artificial Valves," Current Topics in Pathology, 1994, vol. 86, pp. 127-159.

Black et al. "The Sheffield Bicuspid Valve: Concept, Design, and in Vitro and in Vivo Assessment," Biologic Bioprosthetic Valves: Proceedings of the Third International Symposium, 1986, pp. 709-717.

International Preliminary Report on Patentability for International (PCT) Patent Application No. PCT/US2021/042380, dated Feb. 2, 2023 10 pages.

International Search Report prepared by the United States Patent Office on Dec. 21, 2021, for International Application No. PCT/US2021/042380, 4 pgs.

Written Opinion prepared by the United States Patent Office on Dec. 21, 2021, for International Application No. PCT/US2021/042380, 9 pgs.

Official Action for European Patent Application No. 21845838.8, dated Jul. 28, 2025 5 pages.

Official Action for Israel Patent Application No. 299776, dated Jul. 1, 2025 4 pages.

* cited by examiner

SYSTEMS AND METHODS FOR MITRAL VALVE REPLACEMENT

CROSS REFERENCE TO RELATED APPLICATIONS

This application is a national stage application under 35 U.S.C. 371 and claims the benefit of PCT Application No. PCT/US2021/042380, having an international filing date of 20 Jul. 2021, which designated the United States, which PCT application claimed the benefit of U.S. Provisional Patent Application No. 63/054,623, filed 21 Jul. 2020, the entire disclosures of each of which are incorporated herein by reference.

GOVERNMENT RIGHTS

The Government of the United States has certain rights in this invention.

FIELD

The present disclosure relates generally to replacement assemblies for valves in animals. More specifically, various embodiments of the present disclosure provide for methods, systems, and devices for providing replacement heart valves in humans. In preferred embodiments, transcatheter mitral valve implant systems comprising at least one of an implant frame and leaflet(s) are provided.

BACKGROUND

The mitral heart valve lies between the left atrium and left ventricle, allows diastolic filling of the left ventricle from the left atrium, and prevents systolic reflux of left ventricular blood into the left atrium. The native mitral valve consists of two primary scalloped leaflets (anterior and posterior) attached at their base to an ovoid fibrous structure described as an annulus, meeting at leaflet commissural junctions at the annulus, and connected by a network of tendinous chords to primary papillary muscles. There are numerous anatomic variants including secondary leaflets, secondary and false tendinous chordae. The two main (anterior and posterior) mitral leaflets coapt (touch along a central line) during systole and separate widely during diastole. Pathological mitral valve failure is common and caused by primary leaflet degeneration or destruction and by myocardial disease causing secondary malcoaptation of anatomically intact leaflets (in so-called secondary mitral valve regurgitation). The failure modes include combinations of stenosis (impeding diastolic filling) and regurgitation (failure to prevent systolic reflux into the left atrium).

Known systems, methods and devices for transcatheter mitral valves are plagued by energy loss causing flow impedance (mitral stenosis) from comparatively reduced effective orifice area and attenuated intraventricular vortex flow; thrombosis causing thromboembolism such as stroke and degeneration; left ventricular outflow tract obstruction by anterior displacement of the native anterior mitral leaflet or by dynamic obstruction from Bernoulli forces acting on long anterior mitral leaflets; anchoring failure; structural device failure over time; paravalvular leak causing regurgitation mainly related to fixation; among other important shortcomings.

Many of the shortcomings associated with the prior art are related to the three-leaflet (tricuspid/trileaflet) configuration of most investigational transcatheter and marketed surgical bioprosthetic mitral valves, which in turn relates to the decades-long clinical and market dependence on commercial trileaflet surgical and transcatheter heart valves. This market dependence on trileaflet designs relates in part to the manufacturing simplicity of frames having vertical commissural struts or posts underlying all such devices. Known mitral valve replacement systems are shown and described in U.S. Pat. No. 7,591,847 to Navia et al. and U.S. Pat. No. 9,232,996 to Sun et al., which are hereby incorporated by reference in their entireties.

The native human mitral valve comprises a bileaflet design with two main leaflets. The bileaflet structure has numerous advantages including, for example, comparatively reduced flow impedance related to an intrinsically larger effective orifice area. Prototype stented bicuspid bioprosthetic valves, such as the Sheffield valve [Black M, Drury P, Tindale W, A bicuspid bioprosthetic mitral valve. Proc Eur Soc Artif Organs, 1982; 9:116; Black M M, Howard I C, Huang X, Patterson E A, A three-dimensional analysis of a bioprosthetic heart valve. J Biomech, 1991; 24(9):793. [PMID: 1752863]]. exhibit excessive leaflet stress and inadequate orifice area related to vertical stent strut/posts. A key obstacle to bileaflet bioprosthetic mitral valve designs is the complexity of known stent systems that assures leaflet coaptation without prolapse or excessive leaflet stress in an anatomically suitable package. Moreover, in contrast to tri-leaflet prosthetic designs and to the native trileaflet aortic valve, the native mitral valve and chordal apparatus does not rely on longitudinal commissures to support leaflet coaptation without prolapse. Instead the native mitral apparatus relies on chordal insertions into papillary muscles.

SUMMARY

Accordingly, there has been a long-felt but unmet need to provide methods and systems for an improved atrioventricular valve system. Embodiments of the present disclosure are contemplated for use with atrioventricular valve replacement including mitral valve and tricuspid valve replacement applications. It will be recognized, however, that inventive aspects of the present disclosure are not limited to specific valves or intended uses.

While various embodiments of the present disclosure are contemplated for use in mitral valve prosthesis and replacement and are well-suited for such applications, it will be recognized that inventive features, systems, structures, and methods of the present disclosure are not limited to such intended use. Indeed, it is contemplated that various novel and inventive aspects are provided that are not limited to use with the mitral valve, the heart, or even humans. Structures including but not limited to frame and leaflet structures provided herein are contemplated as being useful in other applications and as prosthesis devices for heart and blood valves other than the human mitral valve.

In various embodiments, an arch-like non-strut frame structure as shown and described herein provide chordal support in a bioprosthetic mitral valve system. In some embodiments, a two-part leaflet and frame design for a transcatheter mitral valve bioprosthesis is provided.

It is an object of the present disclosure to provide a frame member for a replacement valve wherein the frame member comprises an elastically deformable member preferably in the form of an arch that is operable to be provided and fit within the interior of the left ventricular cavity (for example). The frame member is preferably deformable to allow adjustment, deformation and/or miniaturization for simple transcatheter/transseptal delivery of the frame and related components. It is contemplated that the frame member is operable to be collapsed and/or lengthened to narrow the device for catheter-delivery. In some embodiments, the frame comprises neochordal attachment sites for receiving and securing leaflets. In some embodiments, the frame member is operable to be oriented posteriorly to impart favorable flow dynamics and avoid or reduce the risk of Bernoulli-type suction causing systolic anterior mitral leaflet motion and valvular regurgitation. In alternative embodiments, a two-arch structure is provided that is operable to provide a chord-free central orifice.

In various embodiments, one or more flexible prosthetic leaflets are provided. Leaflets of the present disclosure preferably comprise a geometry that incorporates neochordal elements that attach to a frame or support structure without requiring commissural posts. The leaflets are provided to prevent systolic prolapse and minimize closure current.

Various implant anchoring solutions are contemplated for use with embodiments of the present disclosure. Embodiments of the present disclosure are contemplated for use with known stent and/or anchoring solutions including, for example, methods and systems for anchoring valves as shown and described in U.S. Pat. No. 9,655,722 to Morriss et al., U.S. Pat. No. 5,332,402 to Teitelbaum, U.S. Patent Application 2008/0221672 to Lamphere et al., and U.S. Patent Application Publication No. 2010/0217382 to Chau et al., U.S. Patent Application Publication No. 2014/0343669 to Lane et al., U.S. Pat. No. 9,387,075 to Bortlein et al., U.S. Pat. No. 10,376,365 to Khairkhahan, which are hereby incorporated by reference in their entireties. One or more of these systems are contemplated for use with the valve systems shown and described herein. It will be recognized, however, that novel aspects for valves and valve systems are provided herewith that are independent from their related or associated anchor(s).

Various embodiments of the present disclosure provide a transcatheter mitral valve replacement ("TMVR") system that is not limited to or provided with any particular anchoring system. As shown and described herein, systems of the present disclosure are contemplated for use with and are operable for use with various anchoring systems. However, the present disclosure and inventive concepts described herein for TMVR are not limited to any particular anchoring or securing system.

In various embodiments, and as shown and described herein, the requirement for commissural posts (such as those provided in a conventional three-leaflet bioprosthetic heart valve) is obviated by the provision of a transcatheter bioprosthetic valve device comprising at least one elastically-deformable mitral-arch cord-attachment structure that is operable to be deformed or compressed for delivery and which is operable to elastically expand after implantation under restoring force.

In various embodiments of the present disclosure, the need for leaflet-attachment commissural valve frame struts is obviated by the provision of biomimetic shrouds (or "chordae" or "neochords") that attach the leaflets to the transcatheter mitral valve frame at attachment points. In some embodiments, the attachment points comprise eyelet-like attachments.

In certain embodiments of the present disclosure, problems of energy loss, thrombosis, and systolic anterior leaflet motion that plague known systems and compromised natural heart valves are mitigated by the provision of a biomimetic bicuspid valve configuration oriented or canted posteriorly toward the apex to impart vorticial rotation onto the left ventricular blood as it enters the mitral inflow, rotates around the apex, and exits the left ventricular outflow tract.

In various embodiments, at least one arch frame is provided that is operable to assume anterior displacement with regard to the mitral annular center of mass, positioned along the native mitral intercomissural line or anteriorly towards the native mitral intertrigonal line. Specifically, in preferred embodiments, an anterior displacement of the arch-like frame is provided upon insertion into the annular fixation component (e.g. stent).

Embodiments of the present disclosure reduce or eliminate the risks of bicuspid bioprosthetic valve leak by providing a quadricuspid configuration for a prosthetic valve member wherein two major (anterior and posterior) and two minor (commissural) leaflets are provided in the valve.

It is an object of the present disclosure to provide an improved valve system wherein bioprosthetic leaflet degeneration, failure, and/or thrombosis are mitigated or eliminated. In some embodiments, a unibody leaflet-chord structure is provided that requires no additional chord-leaflet fixation.

It is another object of embodiments of the present disclosure to address problems associated with broad-bicuspid leaflet prolapse and excessive bicuspid leaflet stress during high-pressure systole. In some embodiments, chordal elements are incorporated along the coapting free edge of the flexible leaflets in biomimetic fashion. The chordal elements are attached at one or more attachment points to a trans-commissural arch-like frame.

It is yet another aspect of the present disclosure to address problems associated with neo-chordal tangling during periodic and non-periodic or chaotic leaflet opening and closing. In some embodiments, secondary chordal attachments are provided between adjacent neochords on flexible leaflets.

In various embodiments, a transcatheter mitral valve frame is provided that comprises at least one metallic arch member and is devoid of commissural struts or posts. The arch member provided attachment point(s) and support for flexible prosthetic mitral valve leaflets. In some embodiments, the leaflets are provided in a "bicuspid" arrangement. The leaflets are contemplated as attaching to the frame both directly (at the base and sides) and indirectly via neochordal elements that connect and attach to the frame.

The arch-like valve frame of various embodiments of the disclosure is preferably elastically deformable into a compressed transcatheter implantation configuration and is expanded into a non-compressed valve configuration for implantation in the mitral valve position. It is contemplated that the frame comprises at least one "capstone" eyelet at the apex of the arch(es) to allow strain-relief during folding into the compressed state. Eyelets and/or additional insertion points on the arch allow attachment of leaflet neochordal elements, and the arch thereby provides countertraction for leaflet opening and closing to control blood flow. The frame arch(es) are designed to be mounted into the frame base asymmetrically such that it is anterior and closer to the aortomitral curtain to accommodate a posterior leaflet occupying the majority of the annular circumference. The arch is preferably inserted and is oriented posteriorly such that the arch extends (from the base to the apex) towards the posterior apex to displace the anterior leaflet away from the left ventricular outflow tract. The frame combines with, or incorporates, other anchoring or fixation mechanisms including but not limited to stent, clamp, and/or anchor members which are represented for the purpose of this invention disclosure in various embodiments and figures as a simple ring. The frame is preferably radiopaque and hemocompatible. Radiopaque features and concepts contemplated for inclusion with embodiments of the present disclosure include but are not limited to those shown and described in U.S. Patent Application Publication No. 2019/0167422 to Guttenberg, which is hereby incorporated by reference in its entirety.

Although not shown in certain Figures, various TMVR anchoring solutions such as centrifugal force stents, wedges, anchors, leaflet-grasps, and similar devices as will be recognized by one of ordinary skill in the art are contemplated for use with systems of the present disclosure.

In some embodiments, it is contemplated that arch frames of the present disclosure comprise a features that span the left ventricular inflow annulus and comprise a height that is approximately twice as great as the radius of the annulus. The arch and base are configured to be oriented parallel to a plane defined by the mitral inter-commissural line and left ventricular apex, and orthogonal to the plane defined by the centers of mass of the mitral annulus, aortic annulus, and left ventricular apex. Frames of the present disclosure preferably attenuate sufficient X-ray photons to allow visualization during imaging including X-ray fluoroscopy. The frames are also preferably fabricated from and/or covered with biocompatible and hemo-compatible material(s).

In alternative embodiments, paired arch frames are provided in a "V" configuration as opposed to a single rounded arch configuration. Such embodiments allow a chord-free major orifice once configured and provided with flexible leaflets. Preferably, devices of the present disclosure are provided with an asymmetric anterior position relative to the annular ring or base member, such that a majority of the ring circumference is occupied by the posterior leaflet.

In certain embodiments, frame members are provided with an angulated posterior orientation of approximately 15-20 degrees with regard to an apex. The arrangement imparts rotation and vorticity to blood inflow and outflow and averts systolic anterior motion of the anterior leaflet and valvular regurgitation caused by pressures and forces created by moving fluid. In embodiments comprising a plurality of arch members, it is contemplated that the orifice or flow path provided by the arches is oriented posteriorly to achieve the same purpose and result.

It is contemplated that the dimensions and height of arches of the present disclosure can be tailored for different leaflet and neochord configurations, as well as dilated and non-dilated target left ventricles. In some embodiments, different leaflet configurations and related frame structures are contemplated. For example, a tetrahedral arch member is contemplated as being provided with a three-leaflet valve member. Additionally, arches that are hinged and do not rely on elastic deformation in order to compress for implantation are contemplated. In some embodiments, an arch or frame member is provided with a pivotable and lockable hinge about which portions of the arch or frame can be rotated for insertion and implantation. It should therefore be recognized that the present disclosure is not limited to the various embodiments shown in the figures.

Embodiments of the present disclosure contemplated providing a transcathether heart valve with leaflet designs to attach to a valve frame. Preferred embodiments are provided as biomimetic prosthetic bicuspid mitral valve leaflets. Preferably, material continuity of the leaflet and neochordae are provided. More specifically, leaflets and neochordae are fashioned from a single sheet or piece of flexible material and wherein excision of empty spaces is provided to form the neochordae elements and valve structure. Preferably, devices are provided with a posterior and an anterior leaflet, and the posterior leaflet is designed to occupy the majority of the circumference of the annular insertions of the anterior and posterior leaflet. The neochordae are preferably clustered distally to ease insertion into valve frame eyelets. The leaflet-neochordal structure preferably comprises a high Reynolds number and disrupts the boundary blood flow layer associated with blood stasis and that contributes to thrombosis.

The leaflet-neochordae structure is preferably affixed to a transcatheter mitral valve arch-like frame, such as those shown and described herein. The base of the frame preferably circumscribes the mitral annulus, and an arch spans between commissural insertions. Leaflet(s) are affixed directly to the base and sides of the frame, and neochordal fixation is to one or more fixation points across the arch.

Leaflet and neochordae structures may be formed from various materials including, for example, fixed pericardial xenografts (bovine, equine, porcine, etc.), template-cut fabric (e.g. polyester and ePTFE). In some embodiments, a plurality of neochordae converge on a leaflet on one end and converge on a single eyelet or attachment point on a second end.

In various embodiments, leaflets and neochordal components are formed from a single sheet of material. In further embodiments, leaflet-neochordae structures are formed from a multiple panels secured or stitched together that impart draught or camber at least when assembled.

In some embodiments, the leaflet structure(s) attach directly to the base of a frame, and neochordae attach to the transcatheter mitral valve frame arch. In other embodiments, the leaflet structure(s) attach directly to the base of the frame and the base of the arch, and neochordae attach to the transcatheter mitral valve frame arch.

In some embodiments, methods to provide a camber, "draught" or 3-dimensional shape to both leaflet and chordal elements is provided by stretching the structure on a curved jig during extracellular matrix cross-linking or "chemical fixation" of bioprosthetic materials such as bovine, equine, porcine pericardium (preferably before fenestration and creation of neochordae).

In one embodiment, a frame member for a mitral valve implant is provided. The frame member comprises an arcuate support member that is deformable between a first position and a second position, wherein the first position comprises a compressed position operable for insertion into the human heart and wherein the second position comprises an expanded position operable for implantation. The arcuate support member extends between a first end and a second end, and at least one of the first end and the second are operable to be secured to at least one of a base member and human tissue. The arcuate support is operable to be provided at an angle relative to an annular plane of a flow path of a mitral valve of the heart.

In one embodiment, a mitral valve implant is provided. The mitral valve implant comprises a support member that is deformable between a first position and a second position, wherein the first position comprises a compressed position operable for insertion into the human heart and wherein the second position comprises an expanded position operable for implantation. The support member extends between a first end and a second end, and at least one of the first end and the second are operable to be secured to at least one of a base member and human tissue. The arcuate support is operable to be provided at an angle relative to an annular plane of a flow path of a mitral valve of the heart. A flexible leaflet member is secured to the support member. The leaflet member comprises at least one fenestration forming a neochordal leaflet extension operable to be secured to the support member. The leaflet member is operable to regulate blood flow through the implant and function as a one-way valve for flow of blood from a left atrium to a left ventricle.

In various embodiments, methods of forming and using devices are provided. In one embodiment, a method of forming a flexible biomimetic bicuspid mitral valve leaflet is provided. The method comprises providing a bioprosthetic material; stretching the bioprosthetic material to achieve a desired biomimetic structure; and performing a cross-link-ing chemical fixation step.

In another embodiment, a method of implanting a frame member for a mitral valve implant is provided. The method comprises providing a frame member with a support mem-ber that is deformable between a first position and a second position, wherein the first position comprises a compressed position operable for insertion into the human heart and wherein the second position comprises an expanded position operable for implantation; applying a force to deform the support member to the first position; inserting the frame member into a mitral annulus of a heart; removing the force and allowing the support member to expand to the second position; securing the frame member in the mitral annulus; and wherein the frame member is secured such that the support member is angled toward a posterior position to enable a desired blood flow.

In preferred embodiments, systems and devices of the present disclosure are inserted or implanted using transseptal catheterization techniques which will be recognized by one of ordinary skill in the art as comprising known techniques for accessing the left atrium of the heart for various purposes including, for example, percutaneous mitral valvuloplasties. Additional techniques, including conventional surgical tech-niques are also contemplated.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exem-plary methods and/or materials are described below. In addition, the materials, methods, and examples are illustra-tive only and are not intended to be necessarily limiting.

DETAILED DESCRIPTION

Figures 1A, 1B:
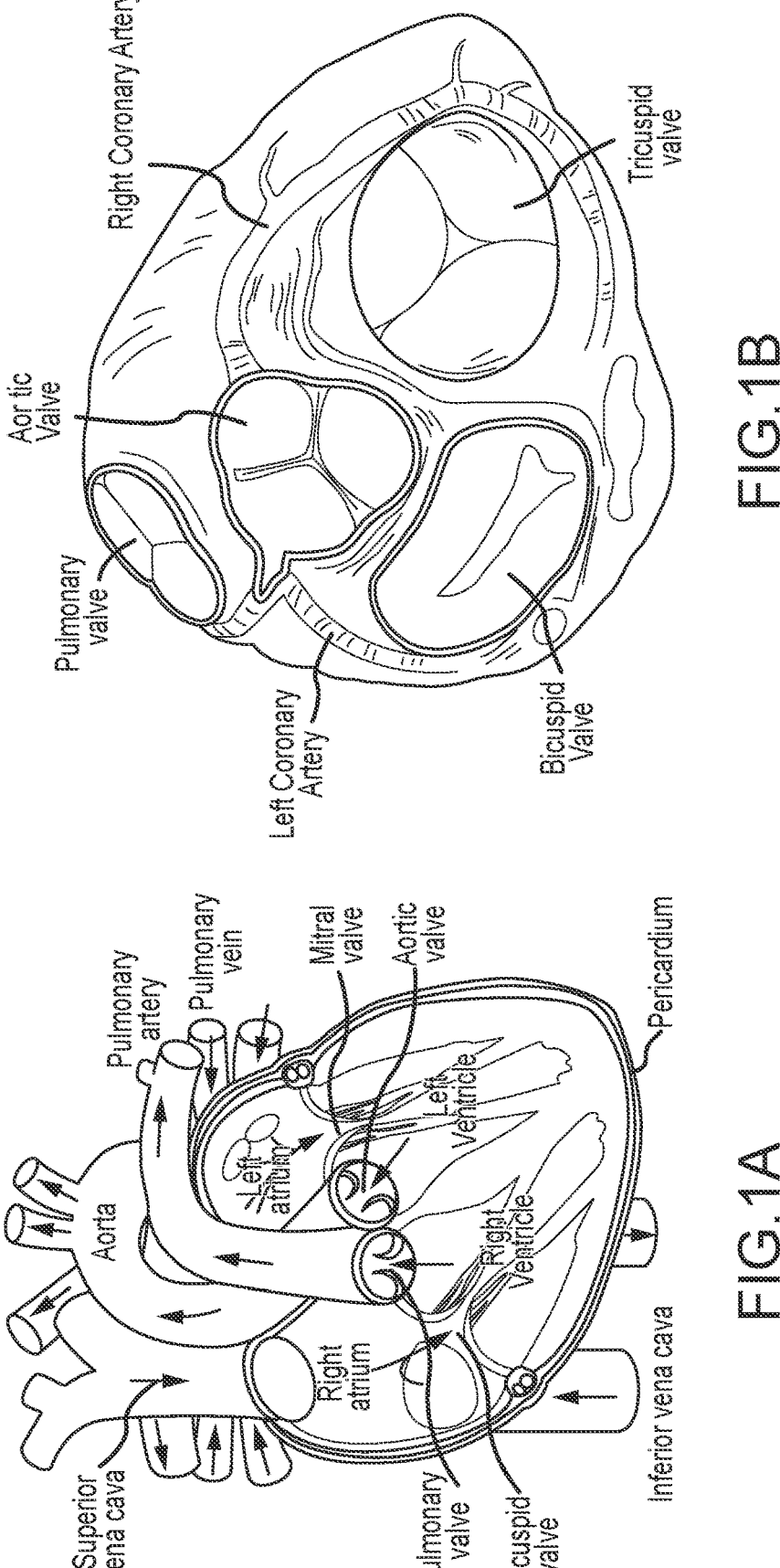
FIG. 1A is a partial cross-sectional view of the anatomy and basic structure of a human heart.
FIG. 1B is a partial cross-sectional view of a human heart.

FIG. 1A is a partial cross-sectional elevation view of a human heart. One of ordinary skill in the art will readily understand the anatomy, structure, and functions of the heart. The mitral valve is provided between the left atrium and the left ventricle, allows diastolic filling of the left ventricle from the left atrium, and prevents systolic reflux of left ventricular blood into the left atrium. The valve is connected to papillary valves via chords. Various embodi-ments of the present disclosure provide systems, methods and devices for replacing a native mitral valve of a human heart. It is contemplated, however, that various novel sys-tems, methods, and devices as shown and described herein may be provided in other applications that are not limited to mitral valve replacement. For example, deformable frame members of the present disclosure may be useful as support structures in various applications and replacement valves.

FIG. 1B is a partial cross-sectional view of the human heart with a native mitral valve depicted and labelled as "bicuspid valve".

Figures 2A, 2B:
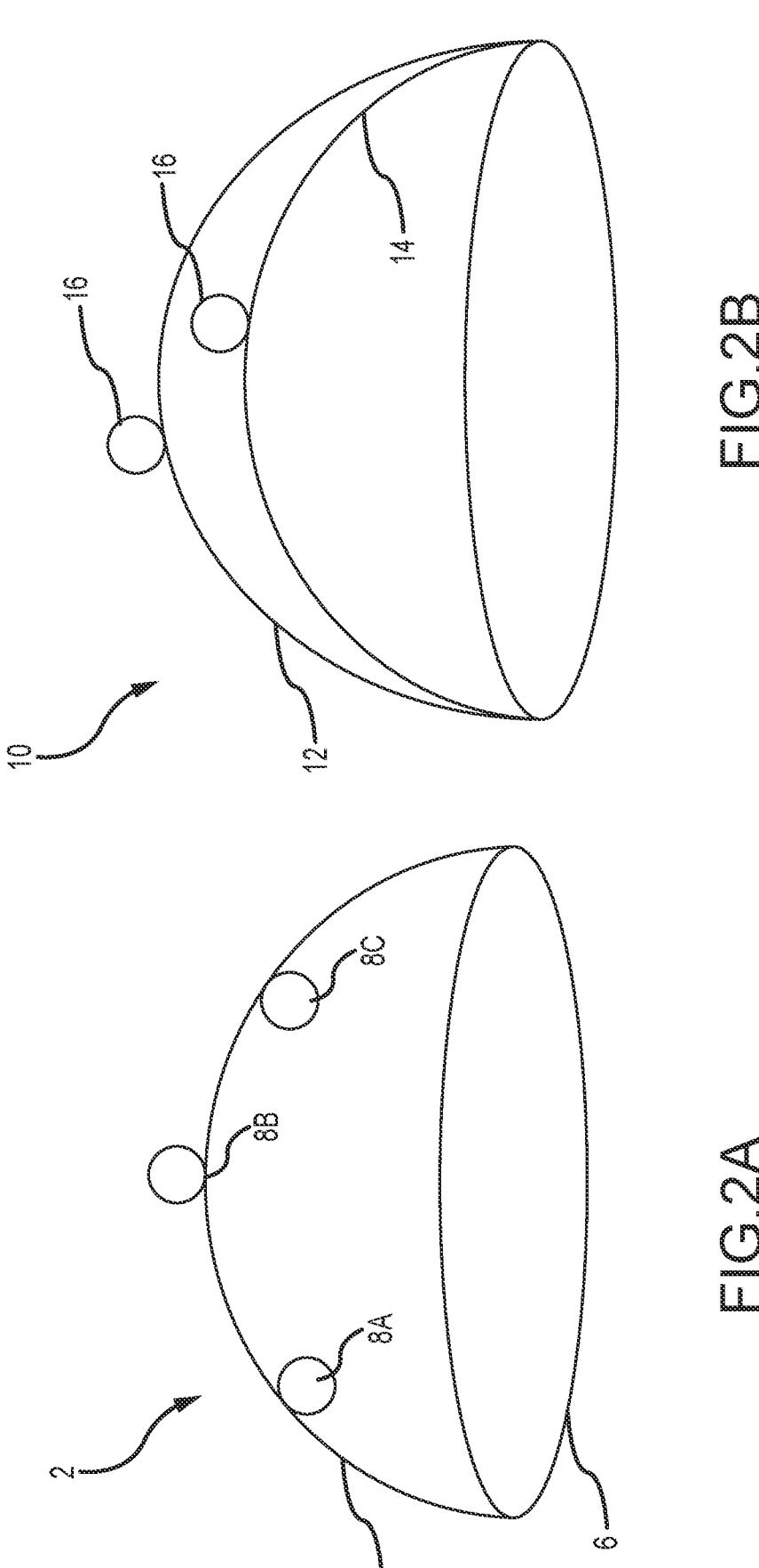
FIG. 2A is an illustration of a frame structure for a valve according to one embodiment of the present disclosure.
FIG. 2B is an illustration of a frame structure for a valve according to one embodiment of the present disclosure.

FIG. 2A is an elevation view of a frame member 2 according to one embodiment of the present disclosure. As shown, the frame member 2 comprises a single arch 4 extending from an annular insert element 6. The frame comprises at least one attachment point 8. In FIGS. 2A-2B, the attachment points are shown as eyelet features. At least one attachment point (8B in FIG. 2A, for example) is contemplated as comprising a flexible strain-relief feature to allow the arch to bend 4 or compress to enable insertion of the device. The attachment points 8A, 8B, 8C further comprise attachment points for bioprosthetic leaflet neo-chordae (8A, 8C in FIG. 2A). The frame member 2 is thus capable of supporting additional features and components of a valve member.

FIG. 2B is an elevation view of a frame member 10 according to yet another embodiment of the present disclo-sure. As shown, the frame member 10 of FIG. 2B comprises a first and second arch 12, 14. Multiple arches are contem-plated to provide a chord-free central valve orifice. Each arch 12, 14 comprises at least one attachment point 16. The attachment points 16 serve to provide a pivot or flexure point to allow the frame to deflect and/or are operable to receive and secure chord members as shown and described herein. Attachment points 8, 16 of the present disclosure are con-templated as being provided on an interior (concave) or exterior (convex) portion of the device. No limitation with respect to the number, spacing, or positioning of the attach-ment points is provided herewith. In some embodiments, an attachment and flexure member (8B, for example) is provided at a center or apex of the arch to efficiently enable flexure and displacement of the arch. In some embodiments, attachment points are provided off-center (8A, 8C, for example).

Frame members of the present disclosure are contemplated as comprising a variety of suitable materials. In some embodiments, arch members of the present disclosure are contemplated as comprising stainless steel, titanium, or other suitable biocompatible metals. Preferably, the frame members comprise an elastic member with a restoring force and wherein the frame member may be compressed for insertion and expand under its own properties when provided in a desired implantation position.

Figures 3A, 3B, 3C:
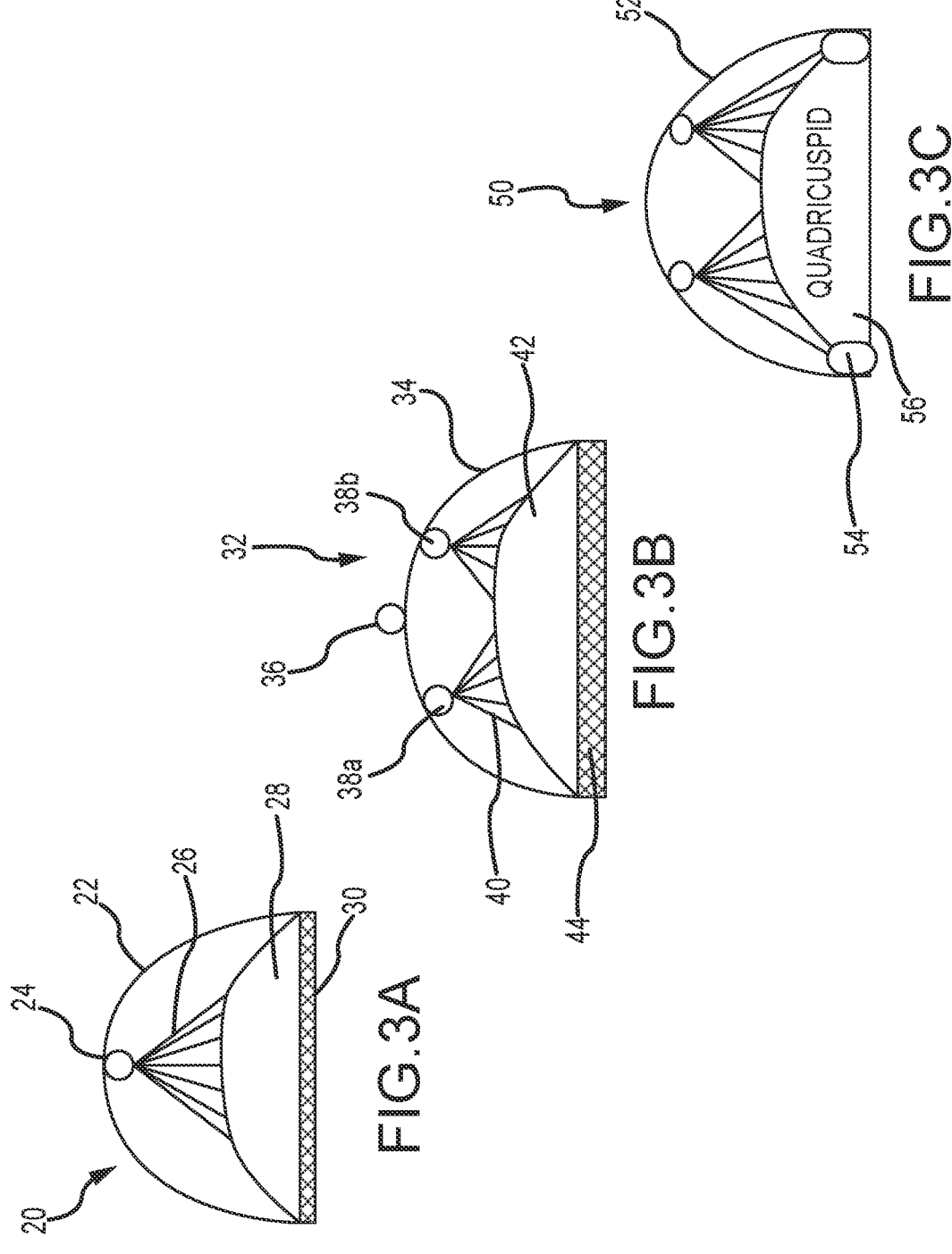
FIG. 3A is an illustration of a frame structure and attached valve elements according to one embodiment of the present disclosure.
FIG. 3B is an illustration of a frame structure and attached valve elements according to one embodiment of the present disclosure.
FIG. 3C is an illustration of a frame structure and attached valve elements according to one embodiment of the present disclosure.

FIG. 3A is an elevation view of a valve element 20 according to one embodiment of the present disclosure. As shown, the valve element 20 comprises an arch member 22 with at least one attachment member 24 for receiving chordal members 26 that extend from at least one leaflet 28 that is operable to control fluid flow through the valve element 20. An annular securing element 30 is provided that is operable to be implanted and secured in a surgical site.

FIG. 3B is an elevation view of one embodiment of the present disclosure wherein a valve element 32 is provided. The valve element 32 comprises an arch 34. A strain relief member 36 is provided at or proximal to an apex of the arch 34. The strain relief member is contemplated as comprising a loop (or multiple loops) in the wireframe arch, and wherein the arch and strain relief member 36 are formed from a single piece of wire or material. Attachment points 38a, 38b are provided as points of attachment for chordal elements 40 that extend from one or more leaflets 42 of the valve 32. The leaflet(s) 42 are attached directly to an annular base 44. In some embodiments, leaflets are secured directly to the arch 34 and wherein edges of the leaflet(s) are secured via the neochordae 40. In certain embodiments, a frame member of the present disclosure comprises a hinge member to fold or adjust the size and shape of the device and wherein the frame does not rely on elastic deformation (or does not rely solely on elastic deformation). For example, in some embodiments, a butterfly hinge is provided to selectively expand and collapse the frame member.

FIG. 3C is an elevation view of a valve element according to another embodiment of the present disclosure. As shown, the valve element 50 of FIG. 3C comprises a quadricuspid arrangement wherein a frame 52 supports minor leaflets 54 at the commissures, as well as major leaflet(s) 56. The minor leaflets 54 can be directly secured to the frame 52 and/or tethered to the supports by neochordae.

Figure 4B:
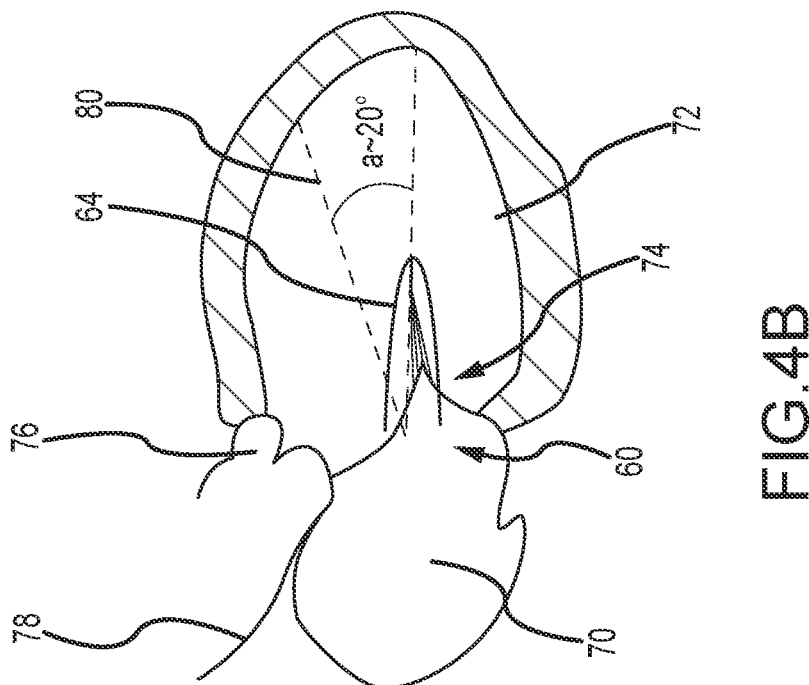
FIG. 4B is a cross-sectional side view of a valve and frame element according to one embodiment of the present disclosure during implantation.
Figure 4A:
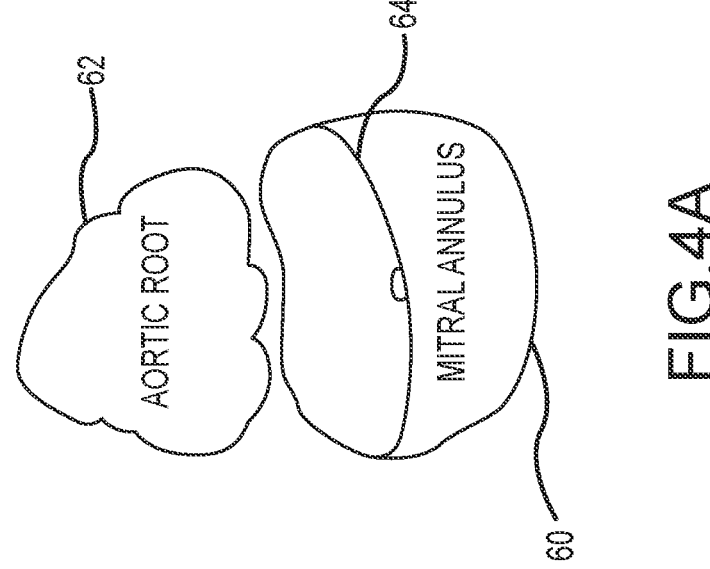
FIG. 4A is a projection of valve according to one embodi-ment of the present disclosure provided in a mitral annulus.

FIG. 4A is a cross-sectional view of the mitral annulus 60 and the aortic root 62 provided adjacent thereto. As shown, an arch 64 is provided in an implanted position in the flow path of the mitral annulus 60. The arch 64 is contemplated as comprising any of the support structures shown and described herein. The arch 64 is preferably angled or canted at angle relative to a longitudinal axis of the mitral annulus. Leaflets and neochordae are omitted from FIG. 4a for illustrative purposes.

FIG. 4B is a 3-chamber side view of a human heart wherein mitral annulus 60 is shown as an annular element between the left atrium 70 and the left ventricle 72. Similar to a native mitral valve, a mitral valve replacement member 74 is provided that comprises a one-way valve between the left atrium 70 and the left ventricle 72 to enable fluid (blood) flow to the ventricle and subsequently out through the aortic valve 76 and the aorta 78. The mitral valve replacement member 74 comprises an arch 64 affixed to the mitral annulus. At least one leaflet member to control and regulate blood-flow is secured to the arch 64. As shown in FIG. 4B, a longitudinal axis 80 of the mitral valve is provided. The arch 64 comprises an angular offset a relative to the longitudinal axis such that the arch (and interconnected leaflets) are not aligned or centered along the longitudinal axis. In various embodiments, the angular offset a is between approximately 5 degrees and approximately 45 degrees. In preferred embodiments, the angular offset a is between approximately 10 degrees and approximately 30 degrees, and more preferably of about 15 degrees and 20 degrees. The arch 64 is preferably angled posteriorly to direct blood flow posteriorly in the ventricle 72 and to approximate the discordant centerlines of the left ventricular and annular principal axes.

Figure 4C:
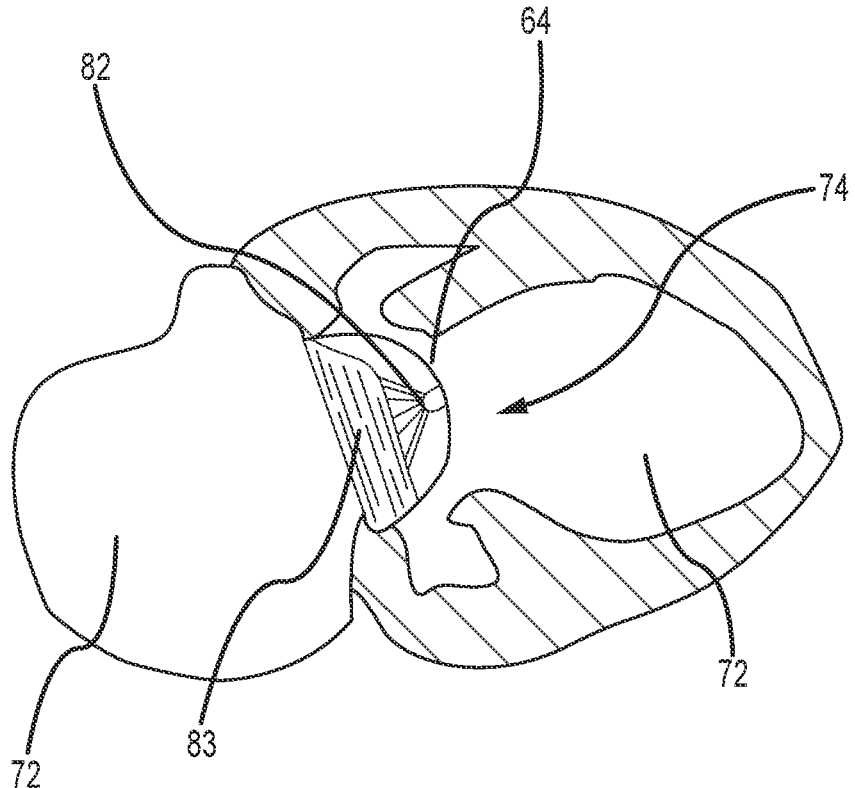
FIG. 4C is a cross-sectional side view of a valve and frame element according to one embodiment of the present disclosure during implantation.

FIG. 4C is a cross-sectional elevation view of the left atrium 70 and left ventricle 72 with a mitral valve replacement member 74 provided therein. As shown, the mitral valve replacement member 74 is provided in an implanted position and comprises an arch 64 extending from commissures of the heart. The arch 64 comprises a structural support with at least one support element 82 that receives and supports neochordae and associated leaflets 83 that are operable to regulate blood flow.

Figure 5:
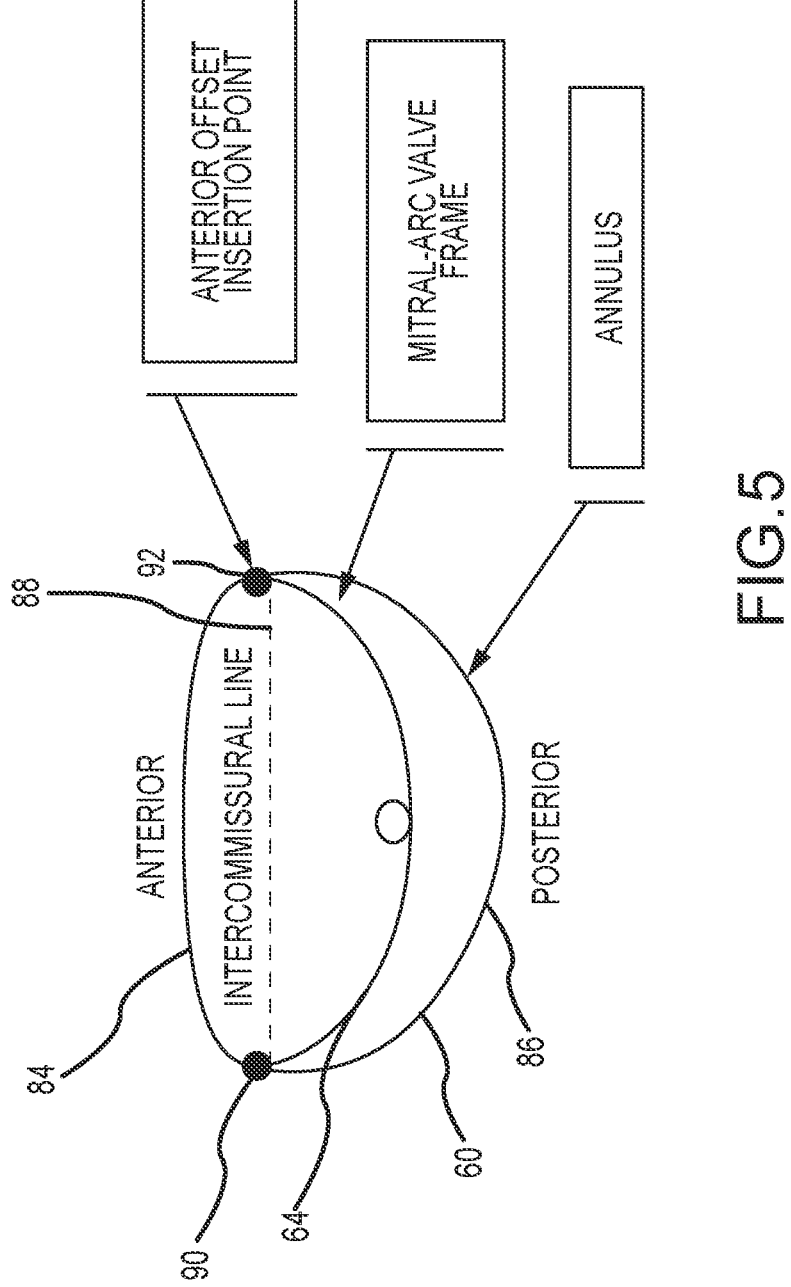
FIG. 5 is a plan view of a mitral annulus and implant feature according to one embodiment of the present disclo-sure.

FIG. 5 is a plan view of a mitral annulus 60 with an arch or frame member 64 in accordance with embodiments of the present disclosure provided therein. As shown, the mitral annulus 60 of the human heart comprises an anterior portion 84 and a posterior portion 86. An intercommissural line 88 extends across the mitral annulus 60 and is depicted in FIG. 5. The frame member 64 comprises a first end 90 and a second end 92, which are each secured to respective sides of the mitral annulus. As shown in FIG. 5, devices and methods of the present disclosure contemplate securing the first and second ends of the frame member 64 in an anterior-offset manner, and wherein the arch and apex of the frame 64 are angled and extend toward the posterior portion 86 of the mitral annulus. As shown in FIG. 5, the frame 64 comprises an eyelet at or proximal to the apex of the arch. The eyelet is operable to serve as a securing or attachment point for leaflet neochordae and/or provides a flexure element to the allow the frame 64 to be compressed for insertion.

Figure 6:
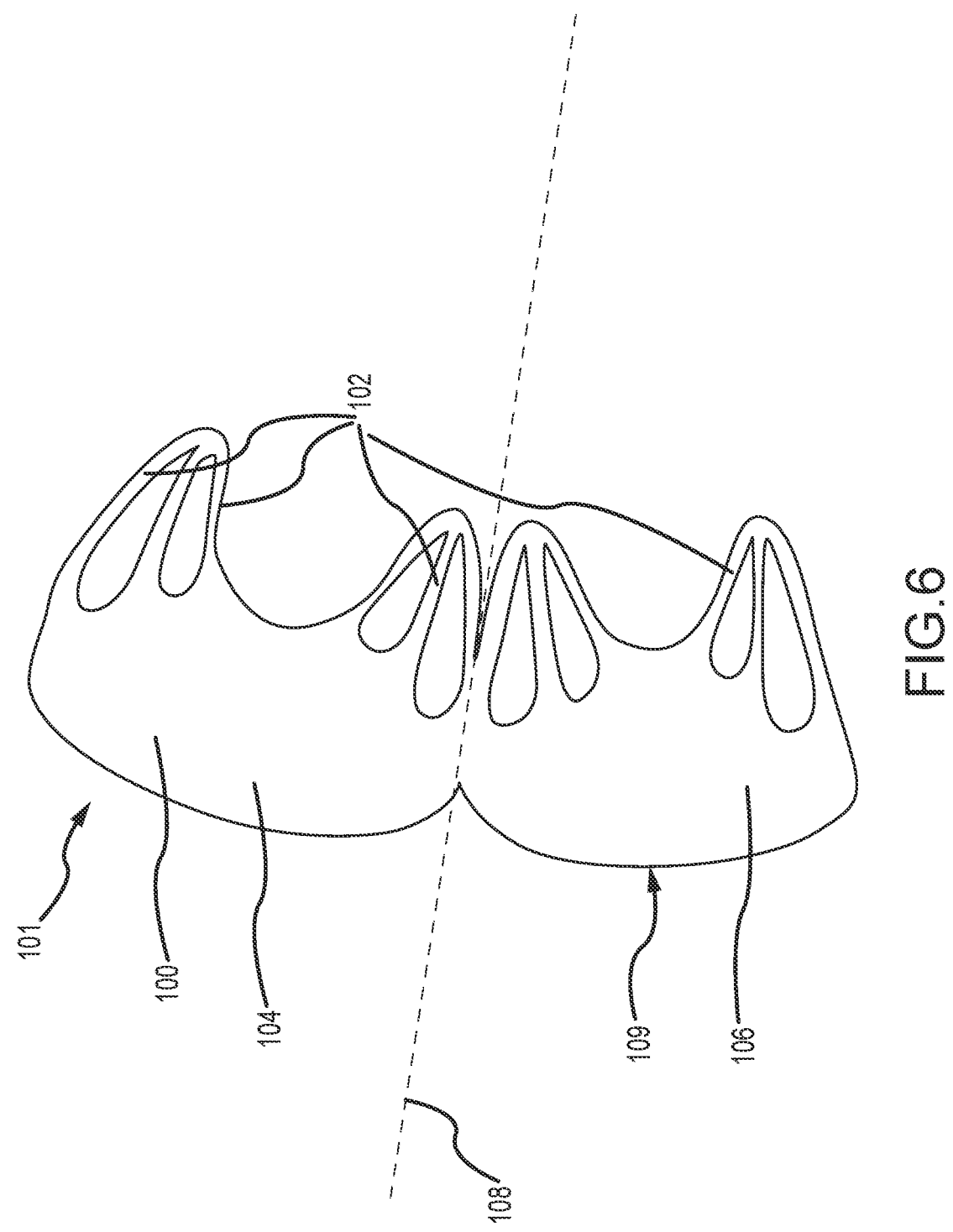
FIG. 6 is a plan view of a leaflet and neochordae structure according to one embodiment of the present disclosure.

FIG. 6 is a side elevation view of a bioprosthetic implant 101 comprising leaflet 100 and neochordae 102 structure according to one embodiment of the present disclosure. The leaflet-neochordae structure is preferably constructed from a single piece of polymeric or bioprosthetic material (e.g. grafts) by fenestrating or excising gaps or voids from the leaflet material to create the neochordae structure 102. The leaflet and neochordae assembly is contemplated as comprising various arrangements including, for example, bicuspid (FIG. 6) and quadricuspid configurations. Distal ends of the neochordae structures 102 are operable to be secured to frame members of the present disclosure and, in combination with the leaflet structure allow for blood to flow through the structure in a diastolic condition (wherein the left ventricle fills with blood) and substantially prevent backflow of blood during a systolic condition (wherein muscle contraction forces blood from the ventricle through the aortic artery).

FIG. 6 shows the implant 101 and leaflet structure 100 in an open and unassembled state. A midline 108 is provided. An anterior portion 104 and a posterior portion 106 of the leaflet are shown. In use and when fully assembly, a base or lower portion 109 of the leaflet is secured to an annular element thereby creating an approximately conical arrangement (see FIG. 7C, for example). As discussed, the assembled device preferably comprises a posterior angle or orientation. Accordingly, leaflet structure 100 of FIG. 6 comprises an asymmetry about the midline 108 wherein the anterior portion 104 comprises a larger surface area than the posterior portion 106.

Figures 7A, 7B, 7C:
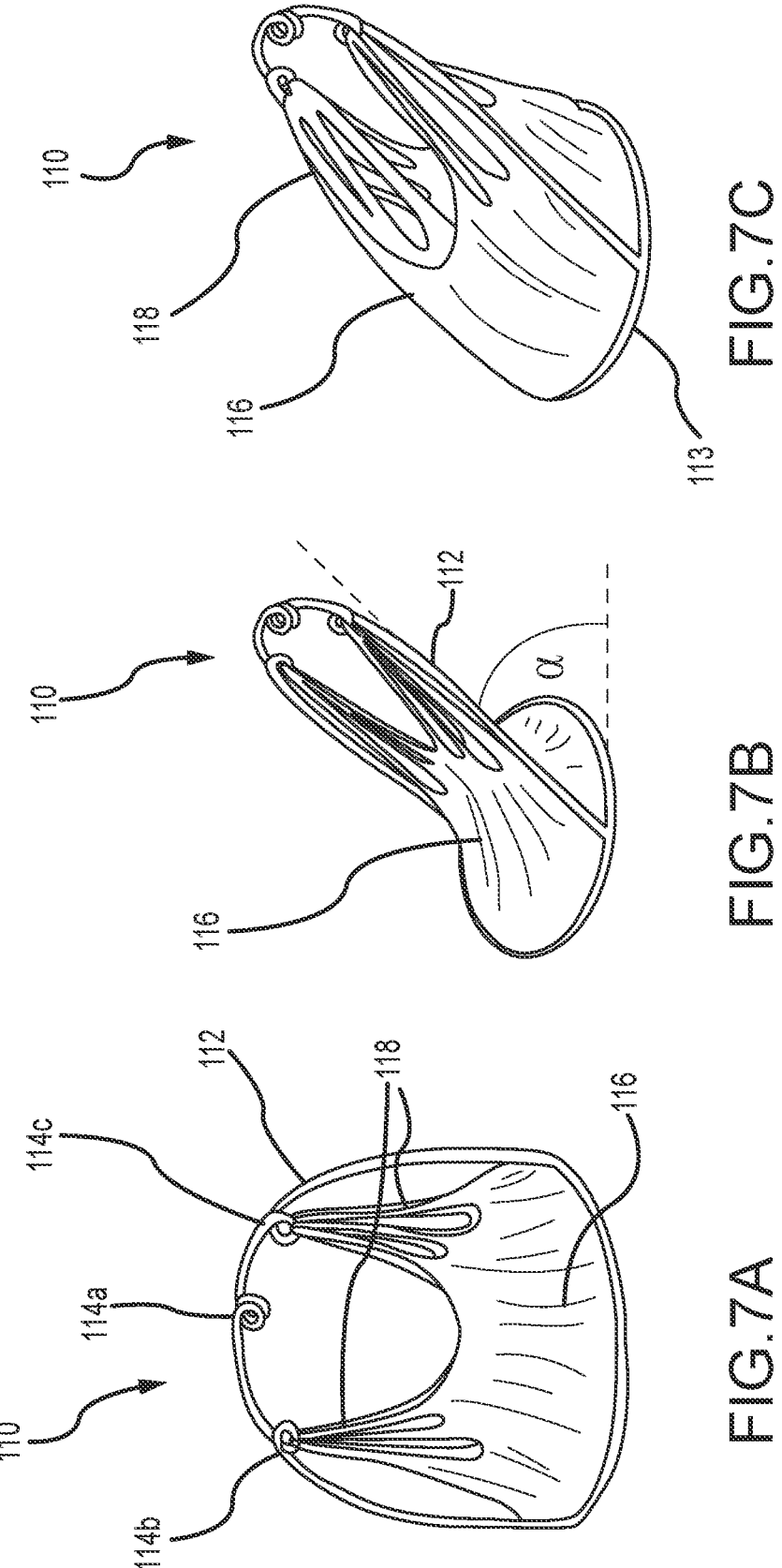
FIG. 7A is a perspective view of a mitral valve implant according to one embodiment of the present disclosure.
FIG. 7B is a perspective view of a mitral valve implant according to one embodiment of the present disclosure.
FIG. 7C is a perspective view of a mitral valve implant according to one embodiment of the present disclosure.

FIG. 7A-7C are elevation views of a mitral valve replacement member 110 according to one embodiment of the present disclosure. As shown, the mitral valve replacement member 110 comprises a member for insertion and implantation with an arch-shaped structural support frame comprising an arch member or arcuate support member 112 and a base member 113. The arcuate support member 112 comprises a plurality of eyelets 114*a*, 114*b*, 114*c*, a leaflet structure 116 and neochordae 118. A first eyelet 114*a* is provided as a strain-relief feature to allow the frame to flex, collapse and elastically restore itself for implantation. Additional eyelets 114*b*, 114*c* are provided as neochordal attachment points. In some embodiments, at least one eyelet is formed by creating a loop or similar deformation in the wire frame. The depicted structure provides for blood flow through the member 110 in a diastolic state (FIG. 7C) and is operable to prevent or minimize an opposite flow of blood during a systolic state (FIG. 7B), thereby mimicking the natural function of a mitral valve. The arcuate support member 112 is preferably provided at an angle α relative to a base member 113 to direct blood flow posteriorly into the left ventricle. In various embodiments, the angle α comprises an angle of between approximately 10 and 70 degrees. In preferred embodiments, the angle α comprises an angle of between approximately 15 and 40 degrees. In some embodiments, the angle α comprises an angle of approximately 20 degrees.

Although certain embodiments provide methods and systems for complete valve replacement, additional embodiments contemplate provide a partial replacement or augmentation of a native valve. For example, in some embodiments, a system of the present disclosure is superimposed over only one dysfunction mitral leaflet, such as the posterior leaflet, and the system coapts with the existing opposite leaflet. In such embodiments, devices, systems, and methods of the present disclosure are operable to be provided as supplemental or partial-replacement systems.

Figure 8:
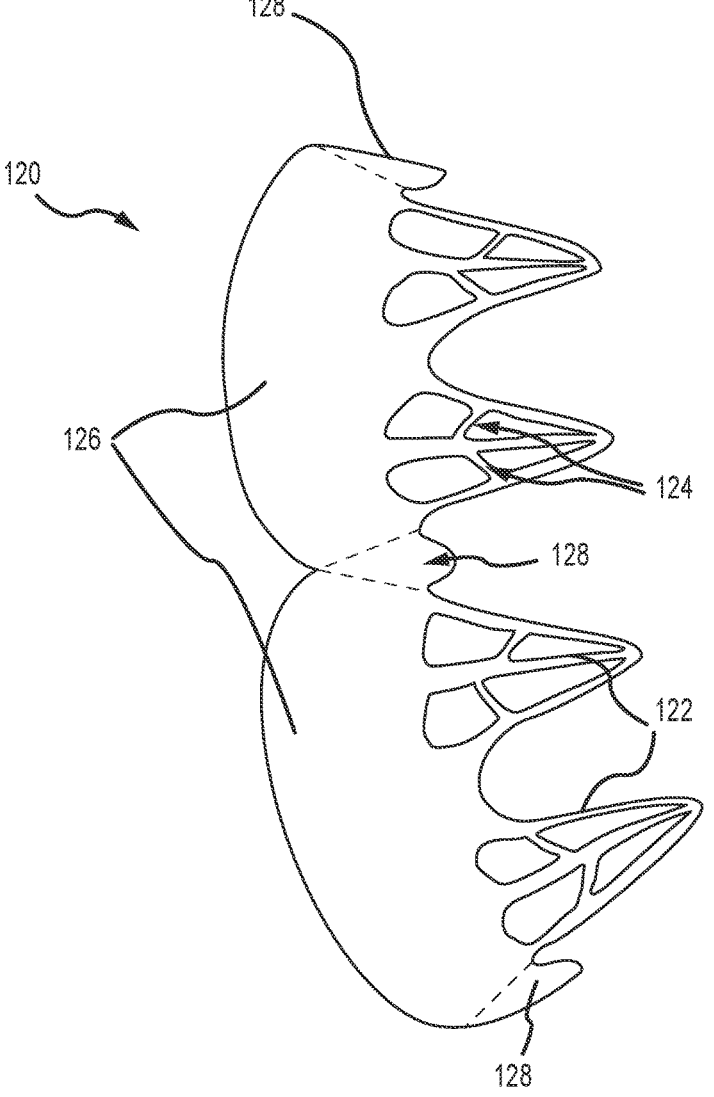
FIG. 8 is a plan view of a leaflet and neochordae structure according to one embodiment of the present disclosure.

FIG. 8 is an elevation view of a leaflet and neochordae structure 120 according to another embodiment of the present disclosure. As shown, the structure 120 comprises a quadricuspid structure with primary leaflets 126 and secondary leaflets 128. Primary neochords 122 are provided and secondary neochords 124 connect adjacent primary neochordae to prevent twisting of the structure without obstructing blood flow. The primary and secondary neochords provide a lattice structure that prevents or reduces the risk of adjacent or parallel neochords becoming tangled or twisted.

As shown in FIG. 8, the structure 120 comprises commissural leaflets 126 to form a quadricuspid bioprosthetic valve configuration. The commissural leaflets 126 are contemplated as comprising neochordal connections to a frame or arch structure (FIG. 3C, for example), and/or may connect to or adjoin the arch structure directly.

It is to be understood that the disclosure is not limited to particular methods or systems, which can, of course, vary. It is also to be understood that the terminology used herein is for the purpose of describing particular embodiments only and is not intended to be limiting.

A number of embodiments of the disclosure have been described. Nevertheless, it will be understood that various modifications may be made without departing from the spirit and scope of the present disclosure. Accordingly, other embodiments are within the scope of the following claims.

What is claimed is:

1. An atrioventricular valve replacement member comprising:
   a structural support member comprising an arcuate support member extending at a non-orthogonal angle from an annular base member;
   the arcuate support member comprising a first end and a second end, and wherein the first end and the second end are secured to the annular base member and wherein at least one of the arcuate support member and the annular base member are operable to be secured to human tissue; and
   wherein at the non-orthogonal angle comprises an angle relative to the base member to direct blood flow at an angle relative to at least the annular base member; and
   wherein the arcuate support member comprises at least one attachment portion for receiving and supporting at least one prosthetic chordal element.

2. The replacement member of claim 1, wherein the arcuate support member comprises a deformable metallic member.

3. The replacement member of claim 1, wherein a prosthetic leaflet structure is secured to the at least one attachment portion.

4. The replacement member of claim 1, wherein the replacement member comprises at least one strain-relief element to enable flexure of the arcuate support member and to enable the arcuate support member to deform between a first position and a second position.

5. The replacement member of claim 4, wherein the strain-relief element comprises at least one of a hinge, a bend or a loop provided in the arcuate support member and wherein a prosthetic chordal element is attached to the strain-relief element.

6. The replacement member of claim 1, wherein the replacement member comprises two arcuate support members.

7. The replacement member of claim 1, wherein the first end and the second of the arcuate support are secured to the annular base member and the base member comprises an annular fixation element operable to be anchored to tissue.

8. The replacement member of claim 1, wherein the non-orthogonal angle comprises and angle between 10 and 70 degrees.

9. An atrioventricular valve implant comprising:
   a support member that is deformable between a first position and a second position, wherein the first position comprises a compressed position operable for insertion into the human heart and wherein the second position comprises an expanded position operable for implantation;
   the support member extending between a first end and a second end, and at least one of the first end and the second are operable to be secured to an annular base member, and wherein the support member comprises an attachment portion further operable to provide a strain-relief feature for the support member;
   a flexible leaflet member secured to the attachment portion;
   the leaflet member being operable to regulate blood flow through the implant and function as a one-way valve.

10. The valve implant of claim 9, wherein the leaflet member comprises a thickness of not more than 2.0 millimeters.

11. The mitral valve implant of claim 9, wherein a plurality of fenestrations are provided to form a fenestrated section and the open fenestrated areas comprise a majority of the fenestrated section.

12. The valve implant of claim 9, wherein primary neo-chordal and secondary neochordal leaflet extensions are provided, and wherein the secondary neochordal leaflet extensions extend in a different direction from the primary neochordal extensions and prevent tangling.

13. The valve implant of claim 9, wherein the arcuate support is operable to be provided at an angle relative to at least one of a plane in which the annular base member resides and an annular plane of a flow path of a mitral valve of the heart.

14. The valve implant of claim 9, wherein the leaflet member comprises at least one fenestration forming a neo-chordal leaflet extension operable to be secured to the support member.

15. A method of forming a flexible biomimetic valve leaflet, the method comprising:

providing a bioprosthetic material;

providing a structural support member comprising an arcuate support member extending at a non-orthogonal angle from an annular base member and wherein the arcuate support member comprises a first end and a second end, and wherein the first end and the second end are secured to the annular base member and wherein at least one of the arcuate support member and the annular base member are operable to be secured to human tissue;

stretching the bioprosthetic material to achieve a desired biomimetic structure relative to the structural support member, and securing the bioprosthetic material to the arcuate support member; and performing a cross-linking chemical fixation step.

16. The method of claim 15, wherein the bioprosthetic material comprises at least one of bovine, equine, or porcine pericardium.

17. The method of claim 15, wherein the step of stretching is performed on a curved jig.

18. The method of claim 15, wherein the step of stretching is performing before and during cross-linking chemical fixation.

19. The method of claim 15, wherein the cross-linking chemical fixation step is performed using at least one of glutaraldehyde, epoxides, and adjunctive anti-calcification strategies.

20. A method of implanting a frame member for an atrioventricular valve implant, the method comprising:

providing a frame member with a support member and an annular base member, the frame member being deform-able between a first position and a second position, wherein the first position comprises a compressed position operable for insertion into the human heart and wherein the second position comprises an expanded position operable for implantation;

applying a force to deform the support member to the first position;

inserting the frame member into a mitral annulus of a heart;

removing the force and allowing the support member to expand to the second position;

securing the frame member to native tissue; and wherein the frame member is secured such that the support member is angled provided at a non-orthogonal angle relative to the annular base member to direct blood flow toward a posterior position.

\* \* \* \* \*